United States Patent
Shalaby

(10) Patent No.: US 8,579,939 B2
(45) Date of Patent: Nov. 12, 2013

(54) SILK / ABSORBABLE POLYESTER HYBRID MEDICAL DEVICES AND APPLICATIONS THEREOF

(75) Inventor: Shalaby W Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 1300 days.

(21) Appl. No.: 11/978,795

(22) Filed: Oct. 30, 2007

(65) Prior Publication Data

US 2008/0103525 A1    May 1, 2008

Related U.S. Application Data

(60) Provisional application No. 60/855,297, filed on Oct. 30, 2006.

(51) Int. Cl.
*A61B 17/04* (2006.01)
*A61L 17/00* (2006.01)

(52) U.S. Cl.
USPC ......................................... 606/230

(58) Field of Classification Search
USPC .............. 606/151, 228–231; 600/37
See application file for complete search history.

(56) References Cited

U.S. PATENT DOCUMENTS

| | | | |
|---|---|---|---|
| 4,461,298 A | 7/1984 | Shalaby | |
| 6,703,035 B2 * | 3/2004 | Shalaby | 424/408 |
| 2006/0085036 A1 * | 4/2006 | Viola | 606/228 |
| 2006/0178701 A1 * | 8/2006 | Schmieding | 606/228 |
| 2006/0240063 A9 * | 10/2006 | Hunter et al. | 424/423 |

OTHER PUBLICATIONS

Fina et al., "The healing of confined critical size cancellous defects in the presence of silk fibroin hydrogel," Biomaterials, 26, (2005), 3527-3536.
Tamada, "New Porcess to Form a Silk Fibroin Porous 3-D Stucture," Biomacromolecules, 6, (2005), 3100-3106.

* cited by examiner

*Primary Examiner* — Melanie Tyson
(74) *Attorney, Agent, or Firm* — McCormick, Paulding & Huber LLP

(57) ABSTRACT

Silk/absorbable polyester hybrid medical devices for tissue repair and regeneration are formed of degummed, naturally produced, multifilament silk yarn in combination with at least one absorbable polyester in the form of a surface coating, with or without an antimicrobial agent, for producing value-added braided silk sutures and multifilament yarn, as well as silk/absorbable polyester fiber composites, for producing tailored hybrid sutures, meshes, and scaffolds for tissue regeneration.

11 Claims, No Drawings

SILK / ABSORBABLE POLYESTER HYBRID MEDICAL DEVICES AND APPLICATIONS THEREOF

The present application claims the benefit of prior provisional application U.S. Ser. No. 60/855,297, filed Oct. 30, 2006.

FIELD OF THE INVENTION

This invention relates to hybrid medical devices made of multifilament, naturally produced silk yarn and at least one synthetic absorbable polyester. A number of products may be formed for use in tissue repair/augmentation, such as surgical sutures and scaffolds for tissue regeneration, exhibiting bimodal or multimodal biological properties.

BACKGROUND OF THE INVENTION

Multifilament silk yarns are made of naturally produced silk. Most, if not all, medical applications of silk multifilament yarn of the prior art have been directed to the production of silk surgical sutures using raw silk multifilament yarn after degumming and often dyeing with black logwood dye. These sutures exhibit excellent mechanical properties due to the exceptionally high tensile strength of small-diameter individual silk fibers. However, commercially available coated silk sutures do suffer from a number of drawbacks, most important of which include (1) the presence of tissue reactive impurities resulting from incomplete degumming of the raw silk yarn; (2) partial loss of tensile strength in wet biological environments due to hydration of the peptide linkages and silk macromolecules; and (3) high tissue reaction to naturally produced components present in major suture coatings, which are used to improve handling and knot tie-down properties. Extensive analysis of these drawbacks has been documented in U.S. Pat. No. 4,461,298 which was directed to composite sutures of multifilament silk embedded in a highly flexible, hydrophobic, highly deformable matrix made of a thermoplastic elastomer. The sutures were claimed to cause minimal irritation in living tissues and retain their strength in vivo for extended periods of time, while retaining the desirable handling qualities of silk. The sutures were prepared by treating commercially available, coated silk braids with a solution of a suitable polymer in a solvent and heating the moving suture through the solution to obtain a continuous impregnation of the silk with the elastomer. However, the polyester component in the specific combination of composite silk suture was a non-absorbable thermoplastic elastomer made of polyether soft segments and aromatic hard segments. Such polyester differs substantially from the absorbable polyesters of the present invention, wherein the polymers are made by the ring-opening polymerization of at least one cyclic monomer. More specifically, the polyester component of the '298 composite performs as a permanent barrier to the silk yarn, while the polyesters subject of this invention are used as a temporary shield or barrier only during the early period of implantation.

Although forms of the silk proteins have been investigated individually relative to their use in treating cancellous defects [*Biomaterials*, 26, 3527 (2005)], and as porous 3-D structures to support cell growth [*Biomacromolecules*, 6, 3100 (2005)] the prior art did not describe the use of silk multifilament in conjunction with synthetic absorbable polyesters as hybrid devices having two modes of degradation—silk degrades proteolytically, while the synthetic polyester degrades/absorbs hydrolytically. And this, in part, provided the incentive to pursue the present invention, which addresses silk/absorbable polyester hybrid devices such as braid silk sutures having an absorbable polyester coating made from at least one cyclic monomer.

SUMMARY OF THE INVENTION

The silk/absorbable polyester hybrid sutures of the present invention are designed to be non-irritating and retain the handling properties of silk sutures, and a higher proportion of the initial mechanical strength in vivo. It is a further object of the present invention to provide a hybrid suture having transient surface barrier properties approaching those of monofilaments and tissue reaction comparable to common synthetic, absorbable sutures. It is a further object of this invention to provide the absorbable polyester to substantially cover the individual silk filaments and having properties such that the polyester, nevertheless, permits the individual components of the silk-based construct to retain most of the initial silk filament flexibility, especially when the construct is a hybrid suture.

Accordingly, this invention is generally directed to a silk/absorbable polyester hybrid device for tissue repair and regeneration which is composed of a multifilament silk textile construct and at least one synthetic absorbable polyester composition.

A specific aspect of this invention deals with a silk/absorbable polyester hybrid device for tissue repair and regeneration which is composed of a multifilament silk textile construct and at least one synthetic absorbable polyester composition, wherein the textile construct is a braided surgical suture and the synthetic absorbable polyester composition is a surface coating for the suture to provide at least two clinically desirable properties selected from the group represented by facile knot tie-down without shattering, adequate in-use knot security, reduced microcapillarity and surface porosity to reduce harboring bacteria and likelihood of infection, minimized tissue drag during surgical procedures, and minimized tissue reaction immediately and at least three (3) days after placement at the surgical site, and wherein the absorbable polyester coating is made by end-grafting an amorphous monocentric, triaxial copolymeric initiator prepared by ring-opening polymerization of about 90 percent by mole of trimethylene carbonate and about 10 percent by mole of F-caprolactone in the presence of stannous octanoate as the catalyst and trimethylolpropane as the initiator, with a mixture of about 95 percent by mole of ε-caprolactone and about 5 percent by mole of 1-lactide.

Meanwhile, the absorbable polyester coating composition represents at least 3 percent by weight of the coated suture. The polyaxial absorbable coating can also contain at least one bioactive agent selected from antimicrobials, cell growth promoting agents, anti-inflammatory drugs, and antineoplastic agents. More specifically, the polyaxial absorbable coating can contain at least one antimicrobial agent. Such antimicrobial agent preferably may be triclosan at a concentration level exceeding 2 percent by weight based on the polyester coating to provide continued release of an effective antimicrobial concentration of triclosan at the surgical site for at least one (1) week.

Another specific aspect of this invention deals with a silk/absorbable polyester hybrid device for tissue repair and regeneration which is a multifilament silk textile construct and at least one synthetic absorbable polyester composition, wherein the multifilament silk textile construct is the core component of a surgical suture braid having a sheath of an absorbable, multifilament yarn made of an absorbable polyester and a lubricous surface coating made of a second absorbable polyester, and wherein the absorbable multifilament sheath of the suture braid is a polyester made from at least one of the cyclic monomers selected from glycolide, l-lactide, trimethylene carbonate, ϵ-caprolactone, p-dioxanone, 1,5-dioxepan-2-one, and a morpholinedione.

A key aspect of this invention deals with a silk/absorbable polyester hybrid device for tissue repair and regeneration which is a multifilament silk textile construct and at least one synthetic absorbable polyester composition, wherein the multifilament silk textile construct is a knitted fabric coated with a synthetic, absorbable, segmented, polyaxial, highly compliant polyester made from at least two cyclic monomers selected from glycolide, l-lactide, trimethylene carbonate, ϵ-caprolactone, p-dioxanone, 1,5-dioxepan-2-one, and a morpholinedione.

Another key aspect of this invention deals with a silk/absorbable polyester hybrid device for tissue repair and regeneration which is a multifilament silk textile construct and at least one synthetic absorbable polyester composition, wherein the multifilament silk construct is a braided construct representing the reinforcing component of a composite having a compliant absorbable matrix of at least one absorbable polyester, thus forming a fiber-reinforced composite, and wherein the fiber-reinforced composite is a ligature for tissue repair or a conformable sheet for tissue regeneration having a fiber to matrix ratio ranging from 95:5 to 20:80.

DETAILED DESCRIPTION OF PREFERRED EMBODIMENTS

For centuries silk fibers have been the gold standard for high quality natural fibers and used for producing quality textile constructs. Interestingly, over the past few decades, silk has maintained its prominence among contemporary synthetic fibers because of the unique properties of the silk single fibers associated with exceptionally high strength and small diameter. As to its use in fibrous medical products, braided silk sutures, for several decades, have been considered the gold standard in terms of knot tie-down and handling characteristics as well as exceptional knot security. While synthetic fibers used in suture manufacturing have found many other applications as medical devices, the use of silk has been practically confined to the production of silk sutures. Accordingly, key aspects of this invention deal with the use of silk in several other medical applications, including surgical meshes and scaffolds for tissue regeneration. Perhaps the limited use of silk for sutures only is associated with the noted high tissue response elicited in the early period of wound repair. This has been associated primarily with the presence of tissue-reactive impurities in the materials used in coating silk sutures. A less obvious source of tissue reactivity may be associated with the incomplete removal of certain reactive impurities present in virgin silk during the degumming process. Accordingly, the present invention deals, in part, with the use of totally synthetic, high-purity polymers which exhibit all the desirable physicochemical attributes of the coating materials used in most coated silk sutures of the prior art without eliciting undesirable tissue reactions. It is also the goal of this invention to provide a reproducible degumming method to secure complete removal of reactive impurities present in virgin silk fibers. As such, uncoated, highly purified silk has been described in this invention as a useful scaffold for tissue regeneration. In some biomedical applications, such as in absorbable sutures, a biodegradable coating is preferred over non-absorbable ones and a key aspect of this invention deals with the use of absorbable polyester coatings for silk sutures and allied products. Another far-from-obvious aspect of this invention deals with silk as slowly biodegradable sutures coated with an absorbable polyester and hence, it can be viewed as a long-lasting, absorbable suture braid. Having silk fibers as highly purified protein materials has been a key aspect of this invention, which deals with the use of silk fibers with other absorbable polyester fibers, wherein the hydrolytic degradation byproducts of the latter accelerate the proteolytic biodegradation of silk. On the other hand, the basic amino acid sequences of the silk molecule act as synthetic enzymes that catalyze the hydrolytic degradation of the polyester chains and hence, absorption of the synthetic fibers. Combinations of silk fibers with at least one synthetic polyester in the form of a coating or fibrous component provides a wide range of applications of purified silk in surgical products other than sutures, including those dealing with tissue regeneration.

Contemporary interest in antimicrobial sutures and allied medical devices, and particularly the controlled delivery type, wherein the antimicrobial agent is incorporated in the coating material, provided the incentive to explore a new dimension in the area of silk/absorbable polyester hybrid devices. More specifically, most of the silk sutures of the prior art are coated with a hydrophobic liquid silicone or a combination of ingredients made primarily of beeswax. These are poor vehicles for use in the single dose and controlled delivery of an antimicrobial agent or agents. Accordingly, this invention deals with a silk/polyester coating as a hybrid device, such as a coated suture, wherein the coating polyester is an excellent vehicle for incorporating the antimicrobial agent and perhaps other bioactive agents for the controlled delivery of such agent or agents. Most interesting is the fact that silk braid can allow the use of exceptionally high levels of coatings and high drug loading without compromising the physicomechanical properties of the braids, and particularly their engineering compliance. Accordingly, the coating and drug levels can be easily modulated to provide a controlled release profile of certain antimicrobial agents for a prolonged period, reaching and exceeding the 3-week period usually required for substantial incisional wound healing.

Further illustrations of the present invention are provided by the following examples:

EXAMPLE 1

Degumming Virgin Silk Yarn as a Multifilament Braid—A Typical Method

A predetermined weight of multifilament silk braid was wound loosely on a set of individual stainless steel wire mesh spools, which allow maximum exposure of the degumming medium. The loaded spools were placed in a water bath of 10 percent high purity soap (such as Ivory® soap) and 1 percent sodium carbonate. The water solution was heated while stirring to insure maximum flow of the solution into the braid construction at 98° C. and kept as this temperature for at least 1 hour. Without cooling, the soap solution was replaced with warm water at a temperature exceeding 40° C. for rinsing residual soap solution. After a second rinsing, the loaded spools were air-dried in a laminar flow hood until constant weight for at least 4 spools in a set of 12 was attained. The spools were weighed then placed in a liquid hydrocarbon bath (e.g., petroleum ether grade 35-60° C.) at room temperature. The liquid was stirred at a sufficient rate to insure maximum flow rate of such liquid into the braid construction for at least 1 hour. The spools were removed and placed in a second rinsing bath. The spools were removed and dried at room temperature in a laminar flow hood and then at 40° C. under reduced pressure for at least 1 hour until a constant weight for 4 spools out of a 12-spool set was attained. The spools were allowed to ready the silk braid for use as a natural product for a logwood dyeing process.

EXAMPLE 2

Preparation of Dyed Silk Braid Using Logwood Dye

Loaded spools from Example 1 were rinsed in a stirred solution of dilute sulfuric acid in water at a concentration of 0.05 M at room temperature for at least 5 minutes. The sulfuric acid solution was then replaced by water to rinse residual acid. The spools were then placed into a stirring water solution of 10 percent nitric acid at 30° C. for at least 1 hour. After rinsing with water, the spools were placed in a stirred water bath at 60° C. for at least 1 hour. The spools were then transferred to a dye solution comprising 10 percent Ivory® soap and 15 percent logwood black dye in water. The solution was heated while stirring to 50° C. and kept at this temperature for at least 20 minutes. The bath temperature was then elevated to 80° C. and the treatment was continued for at least 20 additional minutes. After rinsing with cold water in the usual manner, the spools were placed in a stirring 2 percent solution of sodium dichromate in water and treated for at least 30 minutes. After at least one rinsing with water in the usual manner, the spooled silk braid was first dried in a laminar flow hood for at least 4 hours and then at 40° C. under reduced pressure until a constant weight was attained for 4 spools out of a set of 12. The spooled silk braids were rewound to be ready for coating.

EXAMPLE 3

General Methods of Preparation and Characterization of Crystalline Segmented Polyaxial Copolyesters Using Amorphous Polymeric Initiator and Composition of Representative Polymers General Methods—The procedures described in U.S. Pat. No. 6,462,169, incorporated herein by reference in its entirety, on segmented crystalline copolymer based on amorphous polymeric initiators were adopted for the preparation of this class of polymers in the form of low molecular weight coating materials for use as carriers of the bioactive agents subject of this invention. Accordingly, a polyaxial prepolymer of 90/10 trimethylene carbonate/ε-caprolactone was first prepared using stannous octanoate as the catalyst and triethanolamine or trimethylolpropane as the monomeric initiator at such a stoichiometry so as to form amorphous polymeric initiator i-PX-AN or i-PX-AC, respectively, for end-grafting with a mixture of ε-caprolactone (CL) and glycolide (G) to produce crystalline polyaxial segmented copolyesters PX-ANG and PX-ACG, respectively, or a mixture of ε-caprolactone and l-lactide (l-L) to produce PX-ANL and PX-ACL, respectively, having a weight average molecular weight of 10 to 20 kDa. The resulting polymers, PX-ANG, PX-ACG, PX-ANL, and PX-ACL, were purified by precipitating a concentration acetone solution in cold 2-propanol. After isolation of the polymer by filtration and drying at 25-80° C. to a constant weight under reduced pressure, the purified polymers were then characterized for molecular weight by GPC with dichloromethane (DCM) as the mobile phase, differential scanning calorimetry (DSC) for thermal properties, and infrared for identity.

Representative Polymers-Two representative polymers of type PX-ANG, namely PX-ANG1 and PX-ANG2, were prepared using triethanolamine as the monomeric initiator, stannous octanoate as the catalyst, and a mixture of about 90/10 and about 85/15 trimethylene carbonate/ε-caprolactone (TMC/CL), to prepare the amorphous polymeric initiator i-PX-AN1 and i-PX-AN2, respectively, which were then end-grafted separately with a mixture of about 95/5ε-caprolactone/glycolide (CL/G). Similarly, a representative example of polymer type PX-ACL, namely PX-ACL1, was prepared by first preparing the polymeric initiator i-PX-AC using about a 90/10 mixture of TMC/l-lactide, which was then end-grafted with about a 95/5 mixture of CL/l-L. The three representative copolyesters, PX-ANG1, PX-ANG2, and PX-ACL1, were found to exhibit the following general properties:

$$T_m > 37° C., \Delta H_f > 20 \text{ J/g, and } M_w \leq 20 \text{ kDa}$$

EXAMPLE 4

General Coating Method of a Braided Multifilament Silk Suture and Preparation/Testing of a Representative Antimicrobial Coated Suture General Coating Method—

A concentrated acetone solution of 7 to 20 weight/volume percent of the polyaxial segmented coating PX-ACL1 from Example 3 was prepared. Typically, a suture (from Example 2) was coated by threading through the polymer solution at a controlled rate, depending on the required add-on (5 to 20%). The coated suture was dried in-line by passing through a circulating heated-air oven. Residual acetone was removed by placing the spooled suture in a room-temperature oven under reduced pressure until a constant weight was attained. Depending on the braid size, the dried coated sutures were hot stretched in an air-heated oven at 70° C. using 2 to 4% tension.

Representative Antimicrobial Coated Suture—

A size 2-0 silk braid from Example 2 was coated as described above, with the exception of mixing a concentrated solution of triclosan to the polymer solution. The concentration of the triclosan in solution was varied to provide a different drug dose in the in the final antimicrobial coated suture as noted in Table I.

Testing of the Coated Suture—

The coated sutures were tested for (1) coating percent add-on; (2) knot tie-down; (3) in vitro drug release of antimicrobial agent using HPLC; and (4) in vitro evaluation of antimicrobial activity.

EXAMPLE 5

Evaluation of the Antimicrobial Activities of Triclosan-Containing Coated Silk Sutures Size 2-0 coated silk sutures (from Example 4) containing different triclosan concentrations, as outlined in Table I, were evaluated for their antimicrobial activities against *S. aureus* using the Zone-of-Inhibition method. Results in Table I demonstrate the ability to incorporate different concentrations of triclosan to achieve prolonged antibacterial activity.

TABLE I

Evaluation of Antibacterial Activity of Triclosan-containing Coated 2-0 Silk Sutures[a]

| Suture Number | Coating Add-on on Suture, Wt. % | Triclosan Concentration in Coating, Wt. % | Duration of Activity, Days |
|---|---|---|---|
| 1 | 9.7 | 3 | 21 |
| 2 | 10.8 | 5 | 28 |
| 3 | 8.5 | 7 | >28 |
| 4 | 10 | 10 | >28 |

[a]Using polyaxial coating PX-ACL1 from Example 3 and the Zone-of-Inhibition method.

Preferred embodiments of the invention have been described using specific terms and devices. The words and terms used are for illustrative purposes only. The words and terms are words and terms of description, rather than of limitation. It is to be understood that changes and variations may be made by those of ordinary skill art without departing from the spirit or scope of the invention, which is set forth in the following claims. In addition it should be understood that aspects of the various embodiments may be interchanged in whole or in part. Therefore, the spirit and scope of the appended claims should not be limited to descriptions and examples herein.

What is claimed is:

1. A silk/absorbable polyester hybrid device for tissue repair and regeneration comprising a multifilament silk textile construct and at least one synthetic absorbable polyester composition, the absorbable polyester comprising a triaxial copolyester comprising an amorphous core derived from a monocentric, triaxial initiator comprising trimethylolpropane and a ring-opening polymerization of from about 90 percent by mole of trimethylene carbonate and 10 percent by mole of ε-caprolactone, the amorphous core end-grafted with a mixture of about 95 percent by mole of ε-caprolactone, and about 5 percent by mole of l-lactide.

2. A silk/absorbable polyester hybrid device as set forth in claim 1 wherein the textile construct comprises a braided silk suture and the synthetic absorbable polyester composition comprises a surface coating for said suture.

3. A silk/absorbable polyester hybrid device as set forth in claim 2 wherein the absorbable polyester coating composition represents at least 3 percent of the total coated suture weight.

4. A silk/absorbable polyester hybrid device as set forth in claim 3 wherein the absorbable polyester coating contains at least one bioactive agent selected from the group consisting of antimicrobial agents, cell growth promoting agents, antiinflammatory agents, and antineoplastic agents.

5. A silk/absorbable polyester hybrid device as set forth in claim 4 wherein the absorbable copolyester coating contains at least one antimicrobial agent.

6. A silk/absorbable polyester hybrid device as set forth in claim 5 wherein the antimicrobial agent comprises triclosan at a concentration level of at least about 2 percent of the coating weight.

7. A silk/absorbable polyester hybrid device as set forth in claim 6 wherein the weight percentage of the coating and the weight percentage of the triclosan in the coating are adjusted to provide continued release of an effective antimicrobial concentration of triclosan at a surgical site for at least one (1) week.

8. A silk/absorbable polyester hybrid device as set forth in claim 1 wherein the multifilament silk textile construct comprises a core component of a surgical suture braid, the suture braid further having a sheath comprising an absorbable, multifilament yarn comprising an absorbable polyester and a lubricous surface coating comprising a second absorbable polyester, the lubricous surface coating covering the sheath and core.

9. A silk/absorbable polyester hybrid as set forth in claim 8 wherein the absorbable multifilament sheath comprises a polyester made from at least one cyclic monomer selected from the group consisting of glycolide, 1-lactide, trimethylene carbonate, ε-caprolactone, p-dioxanone, 1,5-dioxepan-2-one, and a morpholinedione.

10. A silk/absorbable polyester hybrid device as set forth in claim 1 comprising a fiber-reinforced composite, wherein the multifilament silk textile construct comprises the reinforcing component of the fiber-reinforced composite and wherein the synthetic, absorbable polyester composition comprises the matrix of the fiber-reinforced composite.

11. A silk/absorbable polyester hybrid device as set forth in claim 10 wherein the fiber-reinforced composite comprises a fiber to matrix ratio from about 95:5 to about 20:80 and is a ligature for tissue repair or a conformable sheet for tissue regeneration.

* * * * *